US008591948B2

(12) United States Patent
Baert et al.

(10) Patent No.: US 8,591,948 B2
(45) Date of Patent: *Nov. 26, 2013

(54) ANTIFUNGAL COMPOSITIONS WITH IMPROVED BIOAVAILABILITY

(75) Inventors: Lieven Elvire Colette Baert, Bruges (BE); Geert Verreck, Malle (BE); Dany Thoné, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 1702 days.

This patent is subject to a terminal disclaimer.

(21) Appl. No.: 11/445,849

(22) Filed: Jun. 1, 2006

(65) Prior Publication Data
US 2006/0263436 A1    Nov. 23, 2006

Related U.S. Application Data

(63) Continuation of application No. 10/218,851, filed on Aug. 14, 2002, now Pat. No. 7,081,255, which is a continuation of application No. 09/194,480, filed as application No. PCT/EP97/02507 on May 12, 1997, now Pat. No. 6,509,038.

(30) Foreign Application Priority Data

May 20, 1996  (EP) .................................. 96201430
Mar. 7, 1997  (EP) .................................. 97200698

(51) Int. Cl.
A61K 9/36    (2006.01)
A61K 9/20    (2006.01)
A61K 9/28    (2006.01)
A61K 9/30    (2006.01)
A61K 31/497  (2006.01)

(52) U.S. Cl.
USPC ........... 424/480; 424/464; 424/474; 424/475; 514/254.07

(58) Field of Classification Search
USPC ............. 424/480, 464, 474, 475; 514/254.07
See application file for complete search history.

(56) References Cited

U.S. PATENT DOCUMENTS

| 5,028,433 A | 7/1991 | Ishimaru et al. | 424/464 |
| 5,340,591 A | 8/1994 | Nakano et al. | 424/499 |
| 5,456,923 A | 10/1995 | Nakamichi et al. | 424/489 |
| 5,461,516 A | 10/1995 | Kawano et al. | 359/890 |
| 5,641,516 A | 6/1997 | Grabowski et al. | 424/489 |
| 5,776,495 A * | 7/1998 | Duclos et al. | 424/455 |

FOREIGN PATENT DOCUMENTS

| DE | 42 26 753 A1 | | 2/1994 |
| EP | 0 012 523 | | 6/1980 |
| FR | 2722984 | * | 2/1996 |
| JP | 07-112928 | * | 5/1995 |
| JP | 08 092 088 | | 4/1996 |
| WO | WO 94/05263 | | 3/1994 |

OTHER PUBLICATIONS

Chiou, W.L. et al., "Pharmaceutical Applications of Solid Dispersion Systems", J. Pharm. Sciences, 1971, 60(9), 1281-1302.
Derwent Publications Abstract, An., 83-59971K/25, 2 pages.
T. Kai, et al., "Oral Absorption Improvement of Poorly Soluble Drug Using Solid Dispersion Technique", Chemical & Pharm Bulletin, 1996, 44(3), 568-571.
Caplus Abstract, AN 1995, 729062, Takei, et al.

* cited by examiner

Primary Examiner — Shengjun Wang
(74) Attorney, Agent, or Firm — Woodcock Washburn LLP

(57) ABSTRACT

The present invention is concerned with novel pharmaceutical compositions of itraconazole which can be administered to a mammal suffering from a fungal infection, whereby a single such dosage form can be administered once daily, and in addition at any time of the day independently of the food taken in by said mammal. These novel compositions comprise particles obtainable by melt-extruding a mixture comprising itraconazole and an appropriate water-soluble polymer and subsequently milling said melt-extruded mixture.

41 Claims, No Drawings

ANTIFUNGAL COMPOSITIONS WITH IMPROVED BIOAVAILABILITY

CROSS-REFERENCE TO RELATED APPLICATIONS

This application is a continuation of application Ser. No. 10/218,851, filed Aug. 14, 2002, now U.S. Pat. No. 7,081,255, which is a continuation of application Ser. No. 09/194,480, filed Nov. 19, 1998, now U.S. Pat. No. 6,509,038, which claims priority under 35 U.S.C. §371 of PCT/EP97/02507 filed May 12, 1997, which claims priority under 35 U.S.C. §119 from EP 96.201.430.4, filed May 20, 1996 and EP 97.200.698.5 filed Mar. 7, 1997, the entireties of which are incorporated herein by reference.

The present invention is concerned with novel pharmaceutical compositions of itraconazole which can be administered to a mammal suffering from a fungal infection, whereby a single such dosage form can be administered once daily, and in addition at any time of the day independently of the food taken in by said mammal. These novel compositions comprise innovative particles obtainable by melt-extruding a mixture comprising itraconazole and an appropriate water-soluble polymer and subsequently milling said melt-extruded mixture.

The development of pharmaceutical compositions having good bioavailability of itraconazole, a compound that is practically insoluble in aqueous media, remains one of the main challenges of pharmaceutical development of this compound.

The term "practically insoluble" or "insoluble" is to be understood as defined in the United States Pharmacopeia, i.e. a "very slightly soluble" compound requiring from 1000 to 10,000 parts of solvent for 1 part of solute; a "practically insoluble" or "insoluble" compound requiring more than 10,000 parts of solvent for 1 part of solute. The solvent referred to herein is water.

Itraconazole or (±)-cis-4-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-2,4-dihydro-2-(1-methylpropyl)-3H-1,2,4-triazol-3-one, is a broadspectrum antifungal compound developed for oral, parenteral and topical use and is disclosed in U.S. Pat. No. 4,267,179. Its difluoro analog, saperconazole or (±)-cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methoxypropyl)-3H-1,2,4-triazol-3-one, has improved activity against *Aspergillus* spp. and is disclosed in U.S. Pat. No. 4,916,134. Both itraconazole and saperconazole consist of a mixture of four diastereoisomers, the preparation and utility of which is disclosed in WO 93/19061: the diastereoisomers of itraconazole and saperconazole are designated [2R-[2α,4α,4(R*)]], [2R-[2α,4α,4(S*)]], [2S-[2α,4α,4(S*)]] and [2S-[2α,4α,4(R*)]]. The term "itraconazole" as used hereinafter is to be interpreted broadly and comprises the free base form and the pharmaceutically acceptable addition salts of itraconazole, or of one of its stereoisomers, or of a mixture of two or three or four of its stereoisomers. The preferred itraconazole compound is the (±)-(2R*,4S*) or (cis) forms of the free base form, having the Chemical Abstracts Registry Number [84625-61-6]. The acid addition forms may be obtained by reaction of the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids such as, for example, acetic, propanoic, hydroxyacetic, 2-hydroxypropanoic, 2-oxopropanoic, ethanedioic, propanedioic, butanedioic, (Z)-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

In WO 94/05263, published on Mar. 17, 1994, there are disclosed beads or pellets having a 25-30 mesh sugar core (600-710 μm) coated with an antifungal, more particularly itraconazole (or saperconazole) and a hydrophilic polymer, more particularly, hydroxypropyl methylcellulose. Finished with a sealing film coat, such cores are referred to as beads or pellets. The beads are filled into capsules suitable for oral administration. The itraconazole is present in the drug-coating and is released readily from the surface of said coated beads, which leads to improved bioavailability of itraconazole (or saperconazole) over the then known oral dosage forms of itraconazole.

The preparation of coated beads as described in WO 94/05263 requires special techniques and special equipment in a purpose-built plant. Indeed, the beads described in the prior art are prepared in a quite complex manner requiring a lot of manipulation steps. First, a drug coating solution is prepared by dissolving into a suitable solvent system appropriate amounts of the antifungal agent and a hydrophilic polymer, preferably hydroxypropyl methylcellulose (HPMC). A suitable solvent system comprises a mixture of methylene chloride and an alcohol. Said mixture should comprise at least 50% by weight of methylene chloride acting as a solvent for the drug substance. As hydroxypropyl methylcellulose does not dissolve completely in methylene chloride, at least 10% alcohol has to be added. Subsequently, the 25-30 mesh sugar cores are drug-coated in a fluidized bed granulator equipped with a bottom spray insert. Not only should the spraying rate be regulated carefully, but also temperature control in the fluidized bed granulator is crucial. Hence, this process requires a lot of control in order to obtain a good quality product reproducibly. Moreover, this technique adequately, but still only partially solves the issue of residual organic solvents, such as methylene chloride and methanol or ethanol, being present in the coating. In order to remove any solvents which might remain in the drug-coated intermediate product, an extra drying step is required. Subsequently, a seal coating is applied and this adds yet another two steps to the production process as it involves another drying step, too.

About 460 mg beads, equivalent to about 100 mg itraconazole, are filled into a hard-gelatin capsule (size 0) and two of these capsules are administered once daily to a patient suffering from a fungal infection. The capsules are commercially available in many countries under the Trademark Sporanox™. In order to achieve the desired antifungal effect, it is essential that the two capsules are ingested at the end of a meal. This may seriously limit how easily the patients can comply with their prescribed therapy; for example, some patients are not able to eat normally or swallow medica-ments easily because of illness, nausea or because of fungal infection of the esophagus. It would therefore be highly desirable to have pharmaceutical dosage forms which can be administered to a patient—or for that matter, to any mammal—at any time of the day independently of food taken in, i.e. dosage forms which can be administered to patients (mammals) in a fasted state. Dosage forms with a high drug content, one unit of which contains the required daily dose of the active ingredient instead of two such units, are another desirable goal in the pharmaceutical development of itraconazole.

At this stage, it may be remarked that therapeutically effective plasma levels of itraconazole can be maintained easily for at least 24 hours as its half-life is sufficiently long. The condition is that the itraconazole must reach the plasma. The absorption of dissolved itraconazole from the stomach is in itself not a problem. Thus, there is no need for a sustained release dosage form of itraconazole, an immediate release form will do just as well. In other words, the main problem with the administration of itraconazole in therapeutically effective amounts is in the first place concerned with ensuring that a sufficient amount of itraconazole remains in solution sufficiently long enough to allow it to get into the circulation, and that it does not convert into a form that is not readily bioavailable, in particular into crystalline itraconazole (which forms, for example, when itraconazole precipitates in an aqueous medium).

The present invention provides pharmaceutical compositions of itraconazole and a water-soluble polymer which can be administered to a mammal, in particular a human, suffering from a fungal infection, whereby a single such dosage form can be administered once daily, and in addition at any time of the day independently of the food taken in by said mammal. The bioavailability of the drug from these dosage forms in fasted and in fed mammals is comparable. The dosage forms can be prepared easily, for example by conventional tabletting techniques. The dosage forms comprise a therapeutically effective amount of novel particles as described in detail hereunder.

Said novel particles consist of a solid dispersion comprising
(a) itraconazole, or one of its stereoisomers, or a mixture of two or three or four of its stereoisomers, and
(b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion will be called "a solid solution" hereinafter. Solid solutions are preferred physical systems because the components therein are usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to particles having domains or small regions wherein amorphous, microcrystalline or crystalline (a), or amorphous, microcrystalline or crystalline (b), or both, are dispersed more or less evenly in another phase comprising (b), or (a), or a solid solution comprising (a) and (b). Said domains are regions within the particles distinctively marked by some physical feature, small in size compared to the size of the particle as a whole, and evenly and randomly distributed throughout the particle. Domains of (a) typically have a size of up to about 25 µm, preferably up to 20 µm.

The particles according to the present invention can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

The melt-extrusion process comprises the following steps:
a) mixing the components (a) and (b),
b) optionally blending additives with the thus obtained mixture,
c) heating the thus obtained blend until one obtains a homogenous melt,
d) forcing the thus obtained melt through one or more nozzles; and
e) cooling the melt till it solidifies.

The terms "melt" and "melting" should be interpreted broadly. For our purposes, these terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

One of the most important parameters of melt extrusion is the temperature at which the melt-extruder is operating. It was found that the operating temperature can easily range between about 120° C. and about 300° C. At temperatures lower than 120° C., itraconazole will not dissolve completely in most water-soluble polymers and the extrudate will not have the required bioavailability. In addition, the process is difficult because of the high viscosity of the mixture. At temperatures of more than 300° C. the water-soluble polymer may decompose to an unacceptable level. It may be noted that there is no need to fear decomposition of itraconazole at temperatures up to 300° C., since this active ingredient is thermally very stable.

The throughput rate is also of importance because even at relatively low temperatures the water-soluble polymer may start to decompose when it remains too long in contact with the heating element.

It will be appreciated that the person skilled in the art will be able to optimize the parameters of the melt extrusion process within the above given ranges. The working temperatures will also be determined by the kind of extruder or the kind of configuration within the extruder that is used. Most of the energy needed to melt, mix and dissolve the components in the extruder can be provided by the heating elements. However, the friction of the material within the extruder may also provide a substantial amount of energy to the mixture and aid in the formation of a homogenous melt of the components.

Spray-drying of a solution of the components also yields a solid dispersion of said components and may be a useful alternative to the melt-extrusion process, particularly in those cases where the water-soluble polymer is not sufficiently stable to withstand the extrusion conditions and where residual solvent can effectively be removed from the solid dispersion. Yet another possible preparation consists of preparing a solution of the components, pouring said solution onto a large surface so as to form a thin film, and evaporating the solvent therefrom.

The solid dispersion product is milled or ground to particles having a particle size of less than 600 µm, preferably less than 400 µm and most preferably less than 125 µm. The particle size proves to be an important factor determining the speed with which tablets having sufficient hardness can be manufactured on a large scale; the smaller the particles, the faster the tabletting speed can be without detrimental effects on their quality. The particle size distribution is such that more than 70% of the particles (measured by weight) have a diameter ranging from about 50 µm to about 500 µM, in particular from about 50 µm to about 200 µm and most in particular from about 50 µm to about 125 µm. Particles of the dimensions mentioned herein can be obtained by sieving them through nominal standard test sieves as described in the CRC Handbook, 64$^{th}$ ed., page F-114. Nominal standard sieves are characterized by the mesh/hole width (µm), DIN 4188 (mm), ASTM E 11-70 (No), Tyler® (mesh) or BS 410 (mesh) values. Throughout this description, and in the claims hereinafter, particle sizes are designated by reference to the mesh/hole width in mm and to the corresponding Sieve No. in the ASTM E11-70 standard.

Preferred are particles wherein the itraconazole is in a non-crystalline phase as these have an intrinsically faster dissolution rate than those wherein part or all of the itraconazole is in a microcrystalline or crystalline form.

Preferably, the solid dispersion is in the form of a solid solution comprising (a) and (b). Alternatively, it may be in the form of a dispersion wherein amorphous or microcrystalline (a) or amorphous or microcrystalline (b) is dispersed more or less evenly in a solid solution comprising (a) and (b).

The water-soluble polymer in the particles according to the present invention is a polymer that has an apparent viscosity of 1 to 100 mPa·s when dissolved in a 2% aqueous solution at 20° C. solution. For example, the water-soluble polymer can be selected from the group comprising
  alkylcelluloses such as methylcellulose,
  hydroxyalkylcelluloses such as hydroxymethylcellulose, hydroxyethylcellulose, hydroxypropylcellulose and hydroxybutylcellulose,
  hydroxyalkyl alkylcelluloses such as hydroxyethyl methylcellulose and hydroxypropyl methylcellulose,
  carboxyalkylcelluloses such as carboxymethylcellulose,
  alkali metal salts of carboxyalkylcelluloses such as sodium carboxymethylcellulose,
  carboxyalkylalkylcelluloses such as carboxymethylethylcellulose,
  carboxyalkylcellulose esters,
  starches,
  pectines such as sodium carboxymethylamylopectine,
  chitin derivates such as chitosan,
  polysaccharides such as alginic acid, alkali metal and ammonium salts thereof, carrageenans, galactomannans, tragacanth, agar-agar, gummi arabicum, guar gummi and xanthan gummi,
  polyacrylic acids and the salts thereof,
  polymethacrylic acids and the salts thereof, methacrylate copolymers,
  polyvinylalcohol,
  polyvinylpyrrolidone, copolymers of polyvinylpyrrolidone with vinyl acetate,
  polyalkylene oxides such as polyethylene oxide and polypropylene oxide and copolymers of ethylene oxide and propylene oxide.

Non-enumerated polymers which are pharmaceutically acceptable and have appropriate physico-chemical properties as defined hereinbefore are equally suited for preparing particles according to the present invention.

Preferred water-soluble polymers are hydroxypropyl methylcelluloses or HPMC. Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxyl groups and the third and fourth digits the approximate percentage composition of hydroxypropoxyl groups; 5 mPa·s is a value indicative of the apparent viscosity of a 2% aqueous solution at 20° C.

The molecular weight of the HPMC normally affects both the release profile of the milled extrudate as well as its physical properties. A desired release profile can thus be designed by choosing an HPMC of an appropriate molecular weight; for immediate release of the active ingredient from the particles, a low molecular weight polymer is preferred. High molecular weight HPMC is more likely to yield a sustained release pharmaceutical dosage form. The molecular weight of a water-soluble cellulose ether is generally expressed in terms of the apparent viscosity at 20° C. of an aqueous solution containing two percent by weight of said polymer. Suitable HPMC include those having a viscosity from about 1 to about 100 mPa·s, in particular form about 3 to about 15 mPa·s, preferably about 5 mPa·s The most preferred type of HPMC having a viscosity of 5 mPa·s, is the commercially available HPMC 2910 5 mPa·s, because this yields particles from which superior oral dosage forms of itraconazole can be prepared as will be discussed hereunder and in the experimental part.

The weight-by-weight ratio of (a):(b) is in the range of 1:1 to 1:17, preferably 1:1 to 1:5. In the case of (itraconazole): (HPMC 2910 5 mPa·s), said ratio may range from about 1:1 to about 1:2, and optimally is about 1:1.5 (or 2:3). The weight by weight ratio of itraconazole to other water-soluble polymers may be determined by a person skilled in the art by straightforward experimentation. The lower limit is determined by practical considerations. Indeed, given the therapeutically effective amount of itraconazole (from about 50 mg to about 300 mg, preferably about 200 mg per day), the lower limit of the ratio is determined by the maximum amount of mixture that can be processed into one dosage form of practical size. When the relative amount of water-soluble polymer is too high, the absolute amount of mixture needed to reach the therapeutic level will be too high to be processed into one capsule or tablet. Tablets, for example, have a maximum weight of about 1 g, and the extrudate can account for maximally about 90% (w/w) thereof. Consequently, the lower limit of the amount of itraconazole over hydroxypropyl methyl cellulose will be about 1:17 (50 mg itraconazole+850 mg water-soluble polymer).

On the other hand, if the ratio is too high, this means the amount of itraconazole is relatively high compared to the amount of water-soluble polymer, then there is the risk that the itraconazole will not dissolve sufficiently in the water-soluble polymer, and thus the required bioavailability will not be obtained. The degree to which a compound has dissolved into a water-soluble polymer can often be checked visually: if the extrudate is clear then it is very likely that the compound will have dissolved completely in the water-soluble polymer. The 1:1 upper limit is determined by the fact that above said ratio it was observed that the extrudate resulting from extruding itraconazole with HPMC 2910 5 mPa·s is not "clear", presumably due to the fact that not all of the itraconazole has dissolved in the HPMC. It will be appreciated that the upper limit of 1:1 may be underestimated for particular water-soluble polymers. Since this can be established easily but for the experimentation time involved, solid dispersions wherein the ratio (a):(b) is larger than 1:1 are also meant to be comprised within the scope of the present invention.

Preferred particles are those obtainable by melt-extrusion of the components and grinding, and optionally sieving. More in particular, the present invention concerns particles consisting of a solid solution comprising two parts by weight of itraconazole and three parts by weight of hydroxypropyl methylcellulose HPMC 2910 5 mPa·s, obtainable by blending said components, melt-extruding the blend at a temperature in the range of 120° C.-300° C., grinding the extrudate, and optionally sieving the thus obtained particles. The preparation is easy to perform and yields itraconazole particles that are free of organic solvent.

The particle as described hereinabove may further comprise one or more pharmaceutically acceptable excipients such as, for example, plasticizers, flavors, colorants, preservatives and the like. Said excipients should not be heat-sensitive, in other words, they should not show any appreciable degradation or decomposition at the working temperature of the melt-extruder.

In the current itraconazole: HPMC 2910 5 mPa·s formulations, the amount of plasticizer is preferably small, in the order of 0% to 15% (w/w), preferably less than 5% (w/w). With other water-soluble polymers though, plasticizers may be employed in much different, often higher amounts because plasticizers as mentioned hereinbelow lower the temperature at which a melt of (a), (b) and plasticizer is formed, and this lowering of the melting point is advantageous where the polymer has limited thermal stability. Suitable plasticizers are pharmaceutically acceptable and include low molecular weight polyalcohols such as ethylene glycol, propylene glycol, 1,2 butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as sorbitol lactate, ethyl lactate, butyl lactate, ethyl glycolate, allyl glycollate; and amines such as monoethanolamine, diethanolamine, triethanolamine, monoisopropanolamine; triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

Once the extrudate is obtained, it is milled and sieved and used as a "normal" ingredient to make pharmaceutical dosage forms.

The particles of the present invention can be formulated into pharmaceutical dosage forms comprising a therapeutically effective amount of particles. Although, at first instance, pharmaceutical dosage forms for oral administration such as tablets and capsules are envisaged, the particles of the present invention can also be used to prepare pharmaceutical dosage forms e.g. for rectal administration. Preferred dosage forms are those adapted for oral administration shaped as a tablet. They can be produced by conventional tabletting techniques with conventional ingredients or excipients and with conventional tabletting machines. In addition, they can be produced at substantially lower cost than the coated cores. As mentioned above, an effective antifungal daily dose of itraconazole ranges from about 50 mg to about 300 mg o.d., and preferably is about 200 mg o.d. When one considers that the weight-by-weight ratio of (a):(b) is maximally about 1:1, then it follows that one dosage form will weigh at least 400 mg. In order to facilitate the swallowing of such a dosage form by a mammal, it is advantageous to give the dosage form, in particular tablets, an appropriate shape. Tablets that can be swallowed comfortably are therefore preferably elongated rather than round in shape. Especially preferred are biconvex oblate tablets. As discussed hereunder in more detail, a film coat on the tablet further contributes to the ease with which it can be swallowed.

Tablets that give an immediate release of itraconazole upon oral ingestion and that have good bioavailability are designed in such a manner that the tablets disintegrate rapidly in the stomach (immediate release) and that the particles which are liberated thereby are kept away from one another so that they do not coalesce, give local high concentrations of itraconazole and the chance that the drug precipitates (bioavailability). The desired effect can be obtained by distributing said particles homogeneously throughout a mixture of a disintegrant and a diluent.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose (crosslinked sodium carboxymethylcellulose). The amount of disintegrant in immediate release tablets according to the present invention may conveniently range from about 3 to about 15% (w/w) and preferably is about 7 to 9%, in particular about 8.5% (w/w). This amount tends to be larger than usual in tablets in order to ensure that the particles are spread over a large volume of the stomach contents upon ingestion. Because disintegrants by their nature yield sustained release formulations when employed in bulk, it is advantageous to dilute them with an inert substance called a diluent or filler.

A variety of materials may be used as diluents or fillers. Examples are spray-dried or anhydrous lactose, sucrose, dextrose, mannitol, sorbitol, starch, cellulose (e.g. micro-crystalline cellulose Avicel™), dihydrated or anhydrous dibasic calcium phosphate, and others known in the art, and mixtures thereof. Preferred is a commercial spray-dried mixture of lactose monohydrate (75%) with microcrystalline cellulose (25%) which is commercially available as Microcelac™. The amount of diluent or filler in the tablets may conveniently range from about 20% to about 40% (w/w) and preferably ranges from about 25% to about 32% (w/w).

The tablet may include a variety of one or more other conventional excipients such as binders, buffering agents, lubricants, glidants, thickening agents, sweetening agents, flavors, and colors. Some excipients can serve multiple purposes.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, talc, mixtures thereof, and others known in the art. Interesting lubricants and glidants are magnesium stearate, and mixtures of magnesium stearate with colloidal silica. A preferred lubricant is hydrogenated vegetable oil type I, most preferably hydrogenated, deodorized Cottonseed oil (commercially available from Karlshamns as Akofine NF™ (formerly called Sterotex™)). Lubricants and glidants generally comprise 0.2 to 7.0% of the total tablet weight.

Other excipients such as coloring agents and pigments may also be added to the tablets of the present invention. Coloring agents and pigments include titanium dioxide and dyes suitable for food. A coloring agent is an optional ingredient in the tablet of the present invention, but when used the coloring agent can be present in an amount up to 3.5% based on the total tablet weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, The amount of flavor may depend on a number of factors including the organoleptic effect desired. Generally the flavor will be present in an amount from about 0% to about 3% (w/w).

As known in the art, tablet blends may be dry-granulated or wet-granulated before tabletting. The tabletting process itself is otherwise standard and readily practised by forming a tablet from desired blend or mixture of ingredients into the appropriate shape using a conventional tablet press.

Tablets of the present invention may further be film-coated to improve taste, to provide ease of swallowing and an elegant appearance. Many suitable polymeric film-coating materials are known in the art. A preferred film-coating material is hydroxypropyl methylcellulose HPMC, especially HPMC 2910 5 mPa·s. Other suitable film-forming polymers also may be used herein, including, hydroxypropylcellulose, and acrylate-methacrylate copolymers. Besides a film-forming polymer, the film coat may further comprise a plasticizer (e.g. propylene glycol) and optionally a pigment (e.g. titanium dioxide). The film-coating suspension also may contain talc as an anti-adhesive. In immediate release tablets according to the invention, the film coat is small and in terms of weight accounts for less than about 3% (w/w) of the total tablet weight.

Preferred dosage forms are those wherein the weight of the particles is at least 40% of the total weight of the total dosage form, that of the diluent ranges from 20 to 40%, and that of the disintegrant ranges from 3 to 10%, the remainder being accounted for by one or more of the excipients described hereinabove. As an example of a preferred oral dosage form comprising 200 mg of itraconazole, the following formula may be given:
  21.65% itraconazole (200 mg)
  32.48% HPMC 2910 5 mPa·s (300 mg)
  30.57% spray-dried lactose monohydrate:microcrystalline cellulose (75:25) mixture (282.4 mg)
  8.49% crospolyvidone (78.4 mg)
  2.79% talc (25.8 mg)
  0.93% hydrogenated vegetable oil Type I (8.6 mg)
  0.28% colloidal anhydrous silica (2.6 mg)
  0.24% magnesium stearate (2.2 mg), yielding
  97.43% tablet core, and
  1.47% HPMC 2910 5 mPa·s (13.57)
  0.37% propyleneglycol (3.39 mg)
  0.29% talc (2.71 mg)
  0.44% titanium dioxide (4.07 mg), yielding
  2.57% film-coat.

Preferred dosage forms according to the present invention are those from which at least 85% of the available itraconazole dissolves within 60 minutes when a dosage form equivalent to 200 mg itraconazole is tested as set forth in USP test <711> in a USP-2 dissolution apparatus under conditions at least as stringent as the following: 900 ml phosphate buffer, pH 6.0, 37° C. with paddles turning at 100 rpm. Tablets complying with the preceding definition can be said to have Q>85% (60'). Preferably, tablets according to the present invention will dissolve faster and have Q>85% (15'), more preferably Q>85% (5').

The present invention further concerns a process of preparing particles as described hereinbefore, characterized by blending the components, extruding said blend at a temperature in the range of 120-300° C., grinding the extrudate, and optionally sieving the particles.

The invention also concerns solid dispersions obtainable by melt-extrusion of
(a) itraconazole or one of its stereoisomers or a mixture of two or three or four of its stereoisomers, and
(b) one or more pharmaceutically acceptable water-soluble polymers.

It is another object of the invention to provide a process of preparing a pharmaceutical dosage form as described hereinbefore, characterized by blending a therapeutically effective amount of particles as described hereinbefore, with pharmaceutically acceptable excipients and compressing said blend into tablets.

Further, this invention concerns particles as described hereinbefore, for use in preparing a pharmaceutical dosage form for oral administration to a mammal suffering from a fungal infection, wherein a single such dosage form can be administered once daily to said mammal.

The invention also relates to particles as described hereinbefore, for use in preparing a pharmaceutical dosage form for oral administration to a mammal suffering from a fungal infection, wherein said dosage form can be administered at any time of the day independently of the food taken in by said mammal.

The present invention also concerns the use of particles according to as described hereinbefore, for the preparation of a pharmaceutical dosage form for oral administration to a mammal suffering from a fungal infection, wherein a single such dosage form can be administered once daily to said mammal.

The present invention also concerns the use of particles as described hereinbefore, for the preparation of a pharmaceutical dosage form for oral administration to a mammal suffering from a fungal infection, wherein said dosage form can be administered at any time of the day independently of the food taken in by said mammal.

The invention also relates to a method of treating a fungal infection in a mammal which comprises administering to said mammal an effective antifingal amount of itraconazole in a single oral dosage form which can be administered once daily.

The invention also relates to a method of treating a fungal infection in a mammal which comprises administering to said mammal an effective antifungal amount of itraconazole in a single oral dosage form which can be administered at any time of the day independently of the food taken in by said mammal.

The invention also relates to a pharmaceutical package suitable for commercial sale comprising a container, an oral dosage form of itraconazole as described hereinbefore, and associated with said package written matter non-limited as to whether the dosage form can be taken with or without food.

It has been observed that the tablets of the present invention showed a remarkably lower food-effect than the prior art Sporanox™ capsules. This means that the difference between taking the medication after a meal or in fasted state is significantly less when the tablet of the present invention is administered than when Sporanox™ capsules are administered. This is of course a huge advantage because the medication can be taken in at any time during the day and is no longer dependent upon the intake of a meal. Moreover, patients, who are feeling nauseous or who are not able to eat can still take the tablets of the present invention.

EXAMPLE 1 a) Preparation of Triaset®

A 40/60 (w/w) mixture of itraconazole (21.74 kg) and hydroxypropyl methylcellulose 2910 5 mPa·s[1] or HPMC 2910 5 mPa·s (32.11 kg) were both sieved and mixed in a planetary mixer until the mixture was homogenous. This physical mixture of itraconazole and HPMC is also known as Triaset®.

b) Preparing the Melt Extrudate 1500 g of Triaset® was fed into a twin screw melt extruder of the type APV-Baker MP19 L/D 15 having the following operating parameters: temperature of the first compartment was 245° C., temperature of the second compartment was 265° C., the twin screw had a rate of 20-300 revolutions/min and was extruded during 120 minutes. The extrudate was brought in a hammer mill of type Fitzmill, the mesh of the sieve was 0.125 inch (=0.32 cm) and revolving speed was 1640 revolutions per minute. The milled extrudate was again brought in a hammer mill, this time with a sieve of mesh 0.063 inch (=0.16 cm) and a revolving speed of 1640 revolutions per minute. Yield was 1169 g (78%).

c) Preparation of a Tabletting Mixture

Microcrystalline cellulose (351 g, 21% (w/w)), Crospovidone (117 g, 7% (w/w)), Aerosil (colloidal silicon dioxide) (5 g, 0.3% (w/w)) and Sterotex (8 g, 0.5% (w/w)) were sieved and mixed together with the milled extrudate (1169 g, 71% (w/w)) using a planetary mixer until a homogenous mixture was obtained (15 minutes).

d) Tabletting

Using the mixture obtained in c) 1450 oval biconvex half-scored tablets of 706 mg (die length=17.6 mm, breadth=8.4 mm) were prepared on an Excenterpress Courtoy 27.

EXAMPLE 2

The process as described in example 1 was repeated, but the extrusion step was carried out as follows:

1000 g of Triaset® was inserted into a meltextruder of the type APV-Baker MP19 L/D 15 having the following operating parameters:temperature of the first compartment was 170° C., temperature of the second compartment was 170° C., the twin screw had a rate of 450 revolutions/min. The extrudate was brought in a hammer mill of type Fitzmill, the mesh of the sieve was 0.125 inch (=0.32 cm) and revolving speed was 1640 revolutions per minute. The milled extrudate was again brought in a hammer mill, this time with a sieve of mesh 0.063 inch (=0.16 cm) and a revolving speed of 1640 revolutions per minute.

The tablets were prepared in the same manner as described in Example 1 and had the following characteristics:
nominal weight: 706 mg
disintegration time: <15 minutes
hardness: >6 daN (deca Newton)
height: 6.7±0.1 mm

EXAMPLE 3

Itraconazole plasma levels in healthy volunteers after single oral administration of 200 mg in two different formulations in fasting conditions.

Treatment with the available prior art itraconazole capsules 200 mg as two 100 mg coated cores-capsules (Sporanox®) in fasting conditions five volunteers

| time (h) | plasma level (ng/ml) mean value (S.D.) |
|---|---|
| 0 | ND[1] |
| 1 | 26.8 (27.1) |
| 2 | 125 (111) |
| 3 | 128 (101) |
| 4 | 110 (84.3) |
| 5 | 84.5 (68.9) |
| 6 | 71.1 (55.2) |
| 8 | 54.5 (44.3) |
| 24 | 25.6 (20.3) |

Treatment with tablets of the present invention as prepared in example 1, i.e one 200 mg "melt extrusion tablet" in fasting conditions

| time (h) | plasma level (ng/ml) mean value (S.D.) |
|---|---|
| 0 | ND[1] |
| 1 | 54.4 (51.3) |
| 2 | 143 (97.8) |
| 3 | 191 (111) |
| 4 | 208 (124) |
| 5 | 198 (136) |
| 6 | 153 (107) |
| 8 | 124 (79) |
| 24 | 44.5 (24.2) |

This limited study in volunteers (n=5) shows that in fasted state the melt extrusion tablet gives a AUC of itraconazole (which is a measure for the bioavailability of itraconazole) that is 2.3 times the AUC of itraconazole when administered as 2 times a 100 mg capsule of Sporanox™. When using the non-parametric test (WILCOXON) this difference appears to be significant at a confidence level of 90%.

EXAMPLE 4 a) Preparation of a Tabletting Mixture

A spray-dried mixture of lactose monohydrate (75%) and microcrystalline cellulose (25%) (2.824 kg, 30.57% (w/w)), Crospovidone (784 g, 8.49% (w/w)), Talc (258 g, 2.79% (w/w)), Aerosil (26 g, 0.28% (w/w)), magnesium stearate (22 g, 0.24% (w/w)) and Sterotex (86 g, 0.093% (w/w)) were sieved and mixed together with the milled extrudate (5 kg, 54.13% (w/w)) using a planetary mixer until a homogenous mixture was obtained (15 minutes). All % (w/w) are based on the total weight of a film-coated tablet.

b) Tabletting

Using the mixture obtained in a) 3,000 oval biconvex tablets of 900 mg were prepared on an Excenterpress Courtoy 27.

c) Film-Coating

The tablets obtained in b) were film-coated using a suspension comprising by weight: HPMC 2910 5 mPa·s (8.5%), propylene glycol (2.1%), talc (1.7%), and titanium dioxide (2.6%) in demineralised water (85%). HPMC 2910 5 mPa·s was added to the purified water and mixed until completely dispersed. The solution was left to stand until clear. Propylene glycol was added and mixed until uniform. Talc and titanium dioxide were added to the solution and mixed until uniform.

The tablets obtained in d) were placed in a coating pan and the pigmented coating solution was sprayed onto the cores. Average tablet weight was 924.7 mg.

d) Packing

The coated tablets were packed into polyvinyl/aluminium foil blister packs, which in turn were packed into cardboard cartons.

e) Dissolution Properties

In-vitro dissolutions studies were performed on the 200 mg tablet formulation. The medium was 900 ml of 0.1 N HCl at 37° C. in Apparatus 2 (USP 23, <711> Dissolution, pp. 1791-1793) (paddle, 100 rpm). The concentration of the active ingredient itraconazole dissolved in the test medium was determined by removing a 3 ml sample at the indicated time, measuring its absorbance at 254 nm and calculating the concentration therefrom.

The following results were obtained:

| Time (min) | Calculated concentration (% w/w) of the active dose | | | | | | |
|---|---|---|---|---|---|---|---|
| | sample 1 | sample 2 | sample 3 | sample 4 | sample 5 | sample 6 | average |
| 0 | 0.00 | 0.00 | 0.00 | 0.00 | 0.00 | 0.00 | 0.00 |
| 5 | 83.70 | 85.10 | 79.56 | 87.39 | 86.04 | 89.73 | 85.25 |
| 15 | 97.65 | 97.79 | 97.34 | 97.20 | 97.29 | 100.62 | 97.98 |
| 30 | 97.43 | 98.78 | 98.82 | 100.71 | 98.82 | 99.59 | 99.02 |
| 45 | 98.42 | 98.55 | 98.69 | 100.49 | 98.87 | 99.18 | 99.03 |
| 60 | 99.27 | 99.54 | 99.36 | 100.44 | 98.91 | 99.23 | 99.46 |

EXAMPLE 5 a) Preparation of Particles <125 μm.

1500 g of Triaset® was melt extruded as as described in example 1 and milled in Fitzmill hammer mill at 4736 rpm and a sieve of 0.51 mm. The particle fraction with a size <125 μm was isolated by further sieving through a sieve No 120 (ASTM E 11-70); yield <10%.

b) Tabletting

A tabletting mixture having a composition as described in Example 4, but comprising particles having a size <125 μm was prepared and compressed on a Korsch tabletting machine operating at a speed of 10,800 tablets/hour, a compression pressure of 1500 to 1950 kg/cm² (147-191.1 MPa). The length of the die was 19 mm, breadth 9.5 mm, and the radius of curvature 9.57 mm. The tablets had the following characteristics:

nominal weight: 906.9 mg
maximum height: 5.88 mm
hardness: 11 daN
disintegration time: 2'15"
friability: 0%

The invention claimed is:

1. A pharmaceutical dosage form comprising:
a therapeutically effective amount of particles having a mean particle size of less than 600 μm consisting of an extrudate which is a solid dispersion or a solid solution obtained by melt extrusion comprising
(a) 5-50 weight percent of itraconazole, or one of its stereoisomers, or a mixture of two or three or four stereoisomers, relative to the weight of the entire particle, in a non-crystalline phase, and
(b) one or more pharmaceutically acceptable water-soluble polymers; and
wherein the particles are homogenously distributed throughout a mixture of a diluent and a disintegrant and the pharmaceutical dosage form is an immediate release tablet.

2. The pharmaceutical dosage form according to claim 1 which is a solid solution comprising (a) and (b).

3. The pharmaceutical dosage form according to claim 1 wherein the water-soluble polymer is selected from the group consisting of
alkylcelluloses,
hydroxyalkylcelluloses,
hydroxyalkyl alkylcelluloses,
starches,
pectines,
chitin derivatives,
polysaccharides, alkali metal and ammonium salts thereof, carrageenans, galactomannans, traganth, agar-agar, gummi arabicum, guar gummi and xanthan gummi,
polyvinylalcohol, and
polyalkylene oxides and copolymers of ethylene oxide and propylene oxide.

4. The pharmaceutical dosage form according to claim 3 wherein the water-soluble polymer is a polymer that has an apparent viscosity of 1 to 100 mPa·s when dissolved in a 2% aqueous solution at 20° C.

5. The pharmaceutical dosage form according to claim 3 wherein the water-soluble polymer is a hydroxyalkyl alkylcellulose.

6. The pharmaceutical dosage form according to claim 5 wherein the water-soluble polymer is hydroxypropyl methylcellulose.

7. The pharmaceutical dosage form according to claim 6 wherein the weight-by-weight ratio of (a):(b) is in the range of 1:1 to 1:17.

8. The pharmaceutical dosage form according to claim 1 wherein the extrudate is a solid solution comprising two parts by weight of (a), to three parts by weight of (b), wherein the one or more pharmaceutically acceptable water-soluble polymers is hydroxypropyl methylcellulose, obtained by blending (a) and (b) to obtain a blend, extruding the blend at a temperature in the range of 120° C.-300° C. to obtain the extrudate, grinding the extrudate, and optionally sieving the thus obtained extrudate.

9. The pharmaceutical dosage form according to claim 1 surrounded by a film-coat comprising a film-forming polymer, a plasticizer and optionally a pigment.

10. The pharmaceutical dosage form according to claim 1 wherein the weight of the particles is at least 40% of the total weight of the pharmaceutical dosage form.

11. The pharmaceutical dosage form according to claim 1 from which at least 85% of the available itraconazole, or one of its stereoisomers, or a mixture of two or three or four of its stereoisomers dissolves within 60 minutes when a dosage form equivalent to 200 mg itraconazole is tested as set forth in USP test <711> in a USP-2 dissolution apparatus under conditions at least as stringent as the following: 900 ml 0.1 N HCl, 37° C. with paddles turning at 100 rpm.

12. A pharmaceutical package suitable for commercial sale comprising a container, the pharmaceutical dosage form as claimed in claim 1, and associated with said package written matter non-limited as to whether the dosage form can be taken with or without food.

13. The pharmaceutical dosage form according to claim 6 wherein the water-soluble polymer is HPMC 2910 5 mPa·s.

14. The pharmaceutical dosage form according to claim 6 wherein the hydroxypropyl methylcellulose has a viscosity of about 3 to about 15 mPa·s.

15. The pharmaceutical dosage form according to claim 1 wherein the mean particle size is less than 400 μm.

16. The pharmaceutical dosage form according to claim 1 wherein the mean particle size is less than 125 μm.

17. The pharmaceutical dosage form according to claim 1 wherein 70 weight percent of the particles have a diameter ranging from 50 μm to 500 μm.

18. The pharmaceutical dosage form according to claim 17 wherein 70 weight percent of the particles have a diameter ranging from 50 μm to 200 μm.

19. The pharmaceutical dosage form according to claim 17 wherein 70 weight percent of the particles have a diameter ranging from 50 μm to 125 μm.

20. The pharmaceutical dosage form according to claim 1 wherein the particles comprise itraconazole, or one of its stereoisomers, or a mixture of two or three or four of its stereoisomers, in the range of 25 to 50 weight percent, relative to the weight of the entire particle.

21. The pharmaceutical dosage form according to claim 1 wherein the tablet comprises from about 50 mg to about 300 mg itraconazole.

22. The pharmaceutical dosage form according to claim 1 wherein the tablet comprises about 200 mg itraconazole.

23. The pharmaceutical dosage form according to claim 1 wherein the weight-by-weight ratio of (a):(b) is in the range of 1:1 to 1:5.

24. The pharmaceutical dosage form according to claim 1 wherein the weight-by-weight ratio of (a):(b) is in the range of about 1:1 to about 1:2.

25. The pharmaceutical dosage form according to claim 1 wherein the weight-by-weight ratio of (a):(b) is about 1:1.5.

26. The package of claim 12 wherein the written matter describes that the dosage form should be taken with food.

27. A pharmaceutical dosage form comprising:
   a therapeutically effective amount of particles having a mean particle size of less than 600 μm consisting of a solid dispersion or solid solution comprising
   (a) 5-50 weight percent of itraconazole, or one of its stereoisomers, or a mixture of two or three or four stereoisomers, relative to the weight of the entire particle, in a non-crystalline phase, and
   (b) one or more pharmaceutically acceptable water-soluble polymers;
   wherein the particles are homogenously distributed throughout a mixture of a diluent and a disintegrant and the pharmaceutical dosage form is an immediate release tablet.

28. The pharmaceutical dosage form according to claim 1 or 27, wherein the diluent comprises spray-dried or anhydrous lactose, sucrose, dextrose, mannitol, sorbitol, starch, cellulose, dihydrated or anhydrous dibasic calcium phosphate, or mixtures thereof.

29. The pharmaceutical dosage form according to claim 1 or 27, wherein the disintegrant is crospovidone, croscarmellose, or a disintegrant that has a coefficient of expansion comparable to crospovidone or croscarmellose.

30. The pharmaceutical dosage form according to claim 1 or 27 wherein the disintegrant is crospovidone, croscarmellose, or a disintegrant that has a coefficient of expansion comparable to crospovidone or croscarmellose, and the diluent is spray-dried or anhydrous lactose, sucrose, dextrose, mannitol, sorbitol, starch, cellulose, dihydrated or anhydrous dibasic calcium phosphate, or mixtures thereof.

31. The pharmaceutical dosage form according to claim 27 from which at least 85% of the available itraconazole, or one of its stereoisomers, or a mixture of two or three or four of its stereoisomers dissolves within 60 minutes when a dosage form equivalent to 200 mg itraconazole is tested as set forth in USP test <711> in a USP-2 dissolution apparatus under conditions at least as stringent as the following: 900 ml 0.1 N HCl, 37° C. with paddles turning at 100 rpm.

32. The pharmaceutical dosage form of claim 1 or 27, wherein the diluent is from 20 to 40% by weight and the disintegrant is from 3 to 10% by weight of the total dosage form.

33. The pharmaceutical dosage form according to claim 27 wherein the one or more pharmaceutically acceptable water-soluble polymers is hydroxypropyl methylcellulose.

34. The pharmaceutical dosage form according to claim 33 wherein the hydroxypropyl methylcellulose has an apparent viscosity of 1 to 100 mPa·s when dissolved in a 2% aqueous solution at 20° C.

35. The pharmaceutical dosage form according to claim 34 wherein the weight-by-weight ratio of (a):(b) is in the range of 1:1 to 1:17.

36. A process of preparing a pharmaceutical dosage form comprising distributing a therapeutically effective amount of particles homogeneously throughout a mixture of a disintegrant and a diluent to obtain a blend and compressing said blend into tablets;
   wherein the particles consist of an extrudate which is a solid dispersion or a solid solution obtained by melt extrusion comprising
   (a) 5-50 weight percent of itraconazole, or one of its stereoisomers, or a mixture of two or three or four stereoisomers, in a non-crystalline phase, and
   (b) one or more pharmaceutically acceptable water-soluble polymers; and wherein the extrudate is milled or ground to particles having a mean particle size of less than 600 μm; and
   wherein the pharmaceutical dosage form is for immediate release of itraconazole upon oral ingestion.

37. The process of claim 36 wherein the extrusion is done at a temperature in the range of about 120° C. to about 300° C.

38. A pharmaceutical dosage form produced by the process of claim 37.

39. The pharmaceutical dosage form according to claim 30 wherein the diluent comprises a spray-dried mixture of lactose monohydrate and microcrystalline cellulose in a 75:25 ratio, and the disintegrant is crospovidone or croscarmellose.

40. A method of treating a fungal infection in a mammal comprising orally administering to the mammal an effective antifungal amount of itraconazole in the pharmaceutical dosage form as claimed in claim 1 or claim 27, wherein said pharmaceutical dosage form can be administered once daily.

41. The method of claim 40, wherein said pharmaceutical dosage form can be administered at any time of day independently of food taken in by said mammal.

* * * * *